United States Patent
Miwa et al.

(10) Patent No.: US 7,455,406 B2
(45) Date of Patent: Nov. 25, 2008

(54) OPHTHALMIC ULTRASONIC DIAGNOSTIC APPARATUS

(75) Inventors: Tetsuyuki Miwa, Nukata-gun (JP); Kazunari Shimizu, Gamagori (JP); Miyuki Ando, Gamagori (JP)

(73) Assignee: Nidek Co., Ltd., Gamagori-shi (JP)

( * ) Notice: Subject to any disclaimer, the term of this patent is extended or adjusted under 35 U.S.C. 154(b) by 0 days.

(21) Appl. No.: 11/905,284

(22) Filed: Sep. 28, 2007

(65) Prior Publication Data
US 2008/0079898 A1 Apr. 3, 2008

(30) Foreign Application Priority Data
Sep. 29, 2006 (JP) .............................. 2006-270139

(51) Int. Cl.
*A61B 3/10* (2006.01)
*A61B 5/05* (2006.01)

(52) U.S. Cl. ...................... 351/205; 600/407

(58) Field of Classification Search ......... 351/205–206, 351/210, 221, 246; 600/407; 601/2
See application file for complete search history.

(56) References Cited

U.S. PATENT DOCUMENTS
4,564,018 A 1/1986 Hutchison et al.
5,029,587 A 7/1991 Baba et al.
6,231,186 B1 5/2001 Broadus et al.
6,652,459 B2 * 11/2003 Payne et al. ................. 600/439
2006/0025685 A1 2/2006 dela Houssaye FOREIGN PATENT DOCUMENTS
JP  A-01-214348  8/1989
JP  A-04-064347  2/1992
JP  A-2001-187022 7/2001
WO  WO 02/07590 A2  1/2002

* cited by examiner

*Primary Examiner*—Scott J. Sugarman
*Assistant Examiner*—Dawayne A Pinkney
(74) *Attorney, Agent, or Firm*—Oliff & Berridge, plc

(57) ABSTRACT

To provide an ophthalmic ultrasonic diagnostic apparatus capable of obtaining measurement result with high reliability without lengthy measurement. The apparatus which measures constituent parts of an eye through A-mode includes an ultrasonic probe for A-mode measurement including a transducer emitting an ultrasonic wave into the eye and receiving reflected echoes from tissues of the parts, calculation means for judging whether signals of the echoes are appropriate and calculating measurement values of the parts based on the signals, a memory storing the calculated values, grouping means for setting grouping ranges having predetermined ranges of permissible dispersion with reference to the measurement values and determining that either the grouping range previously set or the grouping range newly set based on the obtained measurement value remains, and central value calculating means counting the numbers of the measurement values falling within the grouping ranges and calculating a central value based on the measurement values.

8 Claims, 10 Drawing Sheets

| En\Tn | 1 | 2 | 3 | 4 | 5 | 6 | 7 | 8 | 9 | 10 | 11 | 12 | 13 |
|---|---|---|---|---|---|---|---|---|---|---|---|---|---|
| E1  | 1 | 2 | 2 | 2 | 2 | 2 | 2 | 2 | 2 | 2 | 2 | 2 | 2 |
| E2  | X | 2 | 3 | 4 | 4 | 5 | 5 | 5 | 6 | 7 | 7 | 7 | 7 |
| E3  | X | X | 2 | 3 | 4 | 5 | 6 | 7 | 8 | 9 | 9 | 9 | 10 |
| E4  | X | X | X | 3 | 4 | 5 | 5 | 6 | 7 | 8 | 8 | 8 | 8 |
| E5  | X | X | X | X | 3 | 4 | 5 | 6 | 7 | 8 | 8 | 8 | 9 |
| E6  | X | X | X | X | X | 5 | 5 | 6 | 7 | 8 | 8 | 8 | 8 |
| E7  | X | X | X | X | X | X | 3 | 4 | 4 | 4 | 5 | 6 | 7 |
| E8  | X | X | X | X | X | X | X | 6 | 7 | 8 | 8 | 8 | 9 |
| E9  | X | X | X | X | X | X | X | X | 7 | 8 | 8 | 8 | 8 |
| E10 | X | X | X | X | X | X | X | X | X | 8 | 8 | 8 | 8 |
| E11 | X | X | X | X | X | X | X | X | X | X | 2 | 3 | 4 |
| E12 | X | X | X | X | X | X | X | X | X | X | X | 3 | 4 |
| E13 | X | X | X | X | X | X | X | X | X | X | X | X | 7 |

FIG. 8

OPHTHALMIC ULTRASONIC DIAGNOSTIC APPARATUS

BACKGROUND OF THE INVENTION

1. Field of the Invention

The present invention relates to an ophthalmic ultrasonic diagnostic apparatus which diagnoses an eyeball by obtaining information on constituent parts inside the eyeball such as an axial length and a corneal thickness.

2. Description of Related Art

There is known an ophthalmic ultrasonic diagnostic apparatus which obtains information on constituent parts inside an examinee's eye by emitting an ultrasonic wave from an ultrasonic transducer incorporated in a probe and performing processing on echoes reflected respectively from tissues of constituent parts of the eyeball. This apparatus uses the A-mode method by which the reflected echoes from the tissues are displayed as a waveform, and the lengths of the constituent parts such as an axial length and a corneal thickness are calculated (for example, see Japanese Patent Application Unexamined Publication No. 2001-187022).

This kind of apparatus performs automatic measurement in which only a measurement value which falls within a width of permissible dispersion out of sampled results is determined as effective data when the calculated axial length and other lengths are displayed and the measurement is automatically terminated when a predetermined number (e.g. ten) of the effective data is obtained.

A program for the automatic measurement is, for example, set as follows. First, a width of permissible dispersion with reference to a sampled measurement value is determined by the program. Then, if ineffective data that a measurement value falls out of the width is obtained successively three times, the measurement value based on which the width has been initially determined is regarded inappropriate. Then, the measurement values which have been already obtained are abandoned. Then, with reference to a newly sampled measurement value, measurement values which are sampled thereafter are processed in the same manner as above. This is because the program is set based on an idea that the probe generally touches the cornea of the examinee's eye strongly in an early stage of the measurement in which the probe starts to touch the cornea, so that the measurement values of the axial length and the corneal thickness tend to be measured smaller though the measurement values gradually become stable.

However, if a measurer (examiner) is unskilled and cannot make the probe touch the cornea in a stable condition, the measurement values may be dispersed also after the early stage of the measurement, which takes time until the measurement is terminated. Lengthy measurement puts a burden on the examinee and the examiner. A solution to the problem is to reduce the number of conditions for automatic termination (e.g. to reduce the number from ten to three) if the conditions for measurement termination are not satisfied even after a predetermined period of time. However, from the view point of reliability of the measurement result, it is preferable that the number of the conditions is larger.

SUMMARY OF THE INVENTION

An object of the invention is to overcome the problems described above and to provide an ophthalmic ultrasonic diagnostic apparatus capable of obtaining measurement result with high reliability without lengthy measurement.

To achieve the objects and in accordance with the purpose of the present invention, an ophthalmic ultrasonic diagnostic apparatus which measures constituent parts of an examinee's eye through A-mode includes an ultrasonic probe for A-mode measurement including a transducer which emits an ultrasonic wave into the examinee's eye and receives echoes reflected respectively from tissues of the constituent parts, calculation means for judging whether signals of the received reflected echoes are appropriate by analyzing the reflected echo signals and calculating measurement values of the constituent parts based on the reflected echo signals which are judged as appropriate, a memory which stores the calculated measurement values, grouping means for setting grouping ranges having predetermined ranges of permissible dispersion with reference to the measurement values, and determining that either one of the grouping range which is previously set and the grouping range which is newly set based on the obtained measurement value, remains, and central value calculating means for counting the numbers of the measurement values which fall within the respective grouping ranges and calculating a central value based on the measurement values which fall within the grouping range such that the number of the measurement values falling within the grouping range reaches a predetermined number first.

Additional objects and advantages of the invention are set forth in the description which follows, are obvious from the description, or may be learned by practicing the invention. The objects and advantages of the invention may be realized and attained by the apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 8 is a graph showing other measurement results of the second embodiment;

DETAILED DESCRIPTION OF THE PREFERRED EMBODIMENTS

Figure 1:
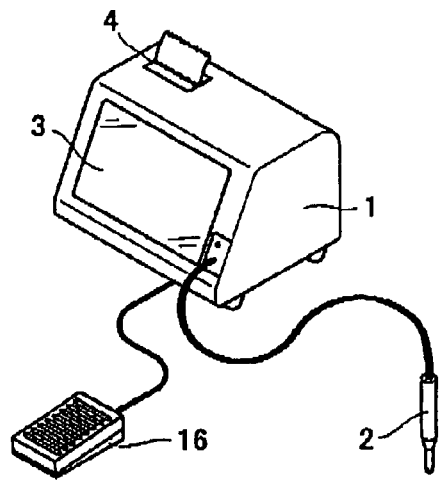
FIG. 1 is an external view of an ophthalmic ultrasonic diagnostic apparatus according to one preferred embodiment of the present invention.
Figure 2:
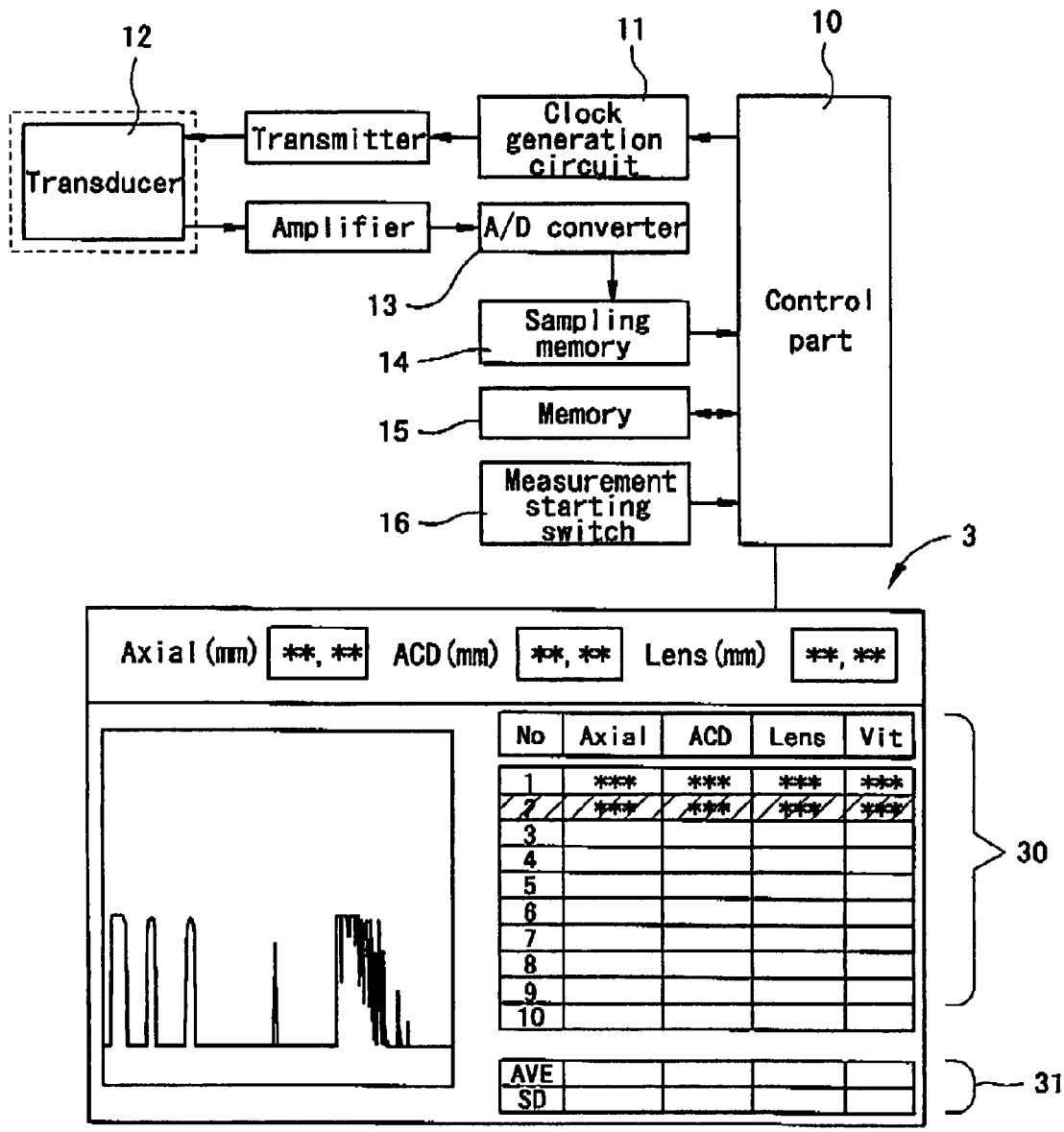
FIG. 2 is a view showing relevant parts of a control part of the ophthalmic ultrasonic diagnostic apparatus.

A detailed description of an ophthalmic ultrasonic diagnostic apparatus which measures an axial length of an eye and other length in the A-mode method according to one preferred embodiment of the present invention is provided below with reference to the accompanying drawings. FIG. 1 is an external view of the ophthalmic ultrasonic diagnostic apparatus according to the preferred embodiment of the present invention. FIG. 2 is a view showing a configuration of relevant parts of a control system of the ophthalmic ultrasonic diagnostic apparatus.

A main body 1 of the apparatus is connected with an ultrasonic probe 2 for A-mode having a transducer 12. In addition, a large liquid crystal display panel 3 capable of color display is provided on a front side of the main body 1. The liquid crystal display panel 3 has a touch panel function. An examiner can set various conditions by performing selecting operation on setup items displayed on the display panel 3. The printer 4 outputs a measurement result.

A control part 10 is included in the main body 1 and controls various circuits. The control part 10 drives and controls a clock generation circuit 11. In addition, the control part 10 controls the transducer 12 incorporated in the probe 2 to emit an ultrasonic wave via a transmitter. At the time of measurement, an operator makes a tip of the probe 2 touch a cornea of an examinee's eye. Echoes reflected respectively from tissues of the eye are received by the transducer 12. Then, the reflected echoes are converted into digital signals by an A/D converter 13 via an amplifier. Information on the reflected echoes converted into the digital signals is stored in a sampling memory 14. The control part 10 samples the reflected echo information at very short intervals. After obtaining waveform data shown in FIG. 3, the control part 10 judges whether or not the waveform data is appropriate. For example, the control part 10 sequentially obtains points CP of intersections of the waveform data and a predetermined threshold value level SL and specifies boundary points BP between the respective constituent parts (a cornea, an anterior chamber, a crystalline lens and a vitreous body). Then, the control part 10 judges (analyzes) whether or not ranges in which the boundary points BP between the respective constituent parts should appear are appropriate. If the reflected echoes are appropriate, the control part 10 which functions as calculation means (a calculation unit) calculates data on the lengths of the respective constituent parts as measurement values. Then, the length data is stored in a memory 15. An axial length of the eye is calculated as the length from a cornea echo to a retina echo. Results of the measurement are displayed on the display panel 3.

In advance of the measurement, the examiner chooses the type of the examinee's eye from items of a phakic eye, an aphakic eye and an eye into which an IOL (intraocular lens) is inserted which are displayed on the display panel 3. In addition, a measurement mode of measuring the axial length, the corneal thickness and other lengths of the constituent parts is selected. In addition, in the measurement of the respective constituent parts, an automatic measurement mode and a manual measurement mode are selectable. In the automatic measurement mode, the control part 10 judges whether or not measurement values and waveform data are appropriate. The measurement is automatically terminated when the predetermined number Np (e.g. ten) of effective data which falls within a measurement value grouping range having a width (range) of permissible dispersion is obtained. In the manual measurement mode, sampling of the measurement values is performed by pushing a measurement starting switch 16. Then, the measurement is terminated when ton measurement results are obtained without judging whether or not the measurement values are effective data.

Hereinafter, a description of an example of an automatic termination program by automatic measurement will be provided. The axial length is taken as an example of a constituent part length to be measured.

First Embodiment of Automatic Termination Program

The first embodiment of the automatic termination program will be described based on a flowchart in FIG. 4 and a graph in FIG. 5. In FIG. 5, the vertical axis indicates the number of measurement for a measurement value of the axial length, and a horizontal axis indicates a measurement value of the axial length. In addition, FIG. 5 is the graph in which measurement results are plotted at every obtainment of the measurement values of the axial length.

Figure 3:
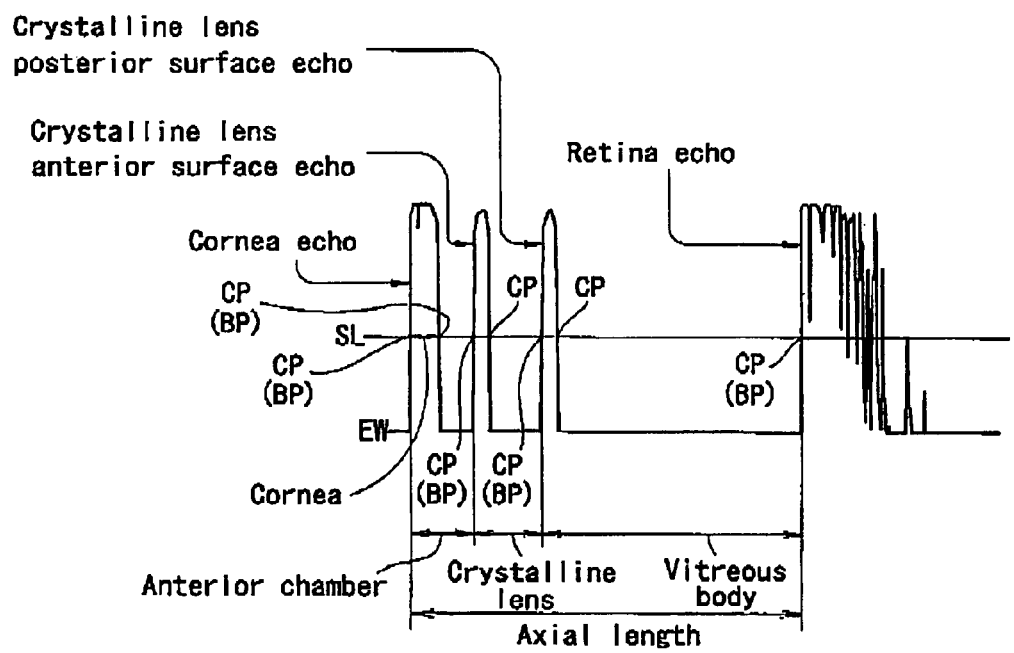
FIG. 3 is a view showing determination of ranges of constituent parts of an eye.

First, the examiner makes the probe 2 touch the cornea of the examinee's eye. Upon the touch, the ultrasonic wave emitted from the transducer 12 is reflected respectively by the tissues inside the examinee's eye, and waveforms of the reflected echoes shown in FIG. 3 are displayed on a screen of the display panel 3. The examiner observes the waveforms of the reflected echoes which are displayed as appropriate so as to adjust the position and the angle of the probe 2 and obtains appropriate waveforms of the reflected echoes, and then pushes the measurement starting switch 16 when an appropriate image is obtained.

The control part 10 receives a trigger signal, and starts sampling of the data stored in the memory 14 (S-1). The control part 10 judges whether or not the obtained waveform data after the sampling is appropriate (S-2). For example, the control part 10 sequentially obtains the points CP of the intersections of the waveform data and the predetermined threshold value level SL so as to specify the boundary points BP between the respective constituent parts (the cornea, the anterior chamber, the crystalline lens and the vitreous body). Then, the control part 10 judges whether or not the boundary points BP between the respective constituent parts are out of the ranges in which the boundary points BP should appear (assumed ranges of the respective constituent parts in a human eye) as shown in FIG. 3. If the boundary points BP between the respective constituent parts fall within the ranges in which the boundary points BP between the respective constituent parts should appear, the waveform data is regarded as appropriate. If the waveform data is not appropriate, the waveform data is deleted (S-4) and new waveform data is obtained after sampling.

When the obtained waveform data after the sampling is appropriate, the control part 10 calculates the measurement value of the axial length. Then, the measurement value is stored in the memory 15 (S-3). Further, the control part 10 which functions as grouping means (a grouping unit) sets a measurement value grouping range (hereinafter, referred to simply as a group) On having a width $\Delta D$ of permissible dispersion with reference to a measurement value $Tn$ ($n=1, 2, 3, \ldots$) of the axial length which is newly stored (the width $\Delta D$ is, for example, a width of $\pm 0.1$ mm taking the measurement value as the center) (S-5). Then, the control part 10 counts the number Nn of the measurement values stored in the memory 15 which fall within the newly set group Dn (S-6). Further, the control part 10 compares the number Nn with the number Nmax of measurement values which fall within a group previously determined as effective data so as to know whether the number Nn is larger than the number Nmax (S-7). If the number Nn is larger than the number Nmax, the effective data is renewed with the measurement values which fall within the newly set group Dn. In addition, the number Nmax is renewed with the number Nn (S-8). The measurement values determined as the effective data are displayed in a display box 30 on the screen of the liquid crystal display panel 3 in FIG. 2 (S-9). Then, when the number Nmax of the effective data reaches the number Np which is a condition for the automatic termination (here, Np is set as ten) (S-10), the measurement is terminated (freezed). Meanwhile, when the number Nn is no larger than the number Nmax in the step S-7, the effective data which falls within the group and was previously determined as the effective data remains as the effective data (S-11).

A specific example by the flowchart in FIG. 4 will be described referring to the measurement results plotted in the graph in FIG. 5. In FIG. 5, the groups On (n=1, 2, . . . ) indicate ranges with the widths ΔD of the permissible dispersion with reference to the measurement values Tn. In addition, the numerics in parentheses right to the measurement values Tn indicate the number Nn of the measurement values which fall within the groups Dn.

A description of a first measurement value T1 of 25.00 mm will be provided. Previous to the measurement value T1, there is no measurement result stored in the memory 15. Accordingly, the number Nn of the measurement value which falls within a group D1 set with reference to the measurement value T1 is one. Then, the measurement value T1 in the group D1 is determined as affective data in the step S-7 and the step S-8. The number Nmax is one, and the measurement value is displayed in the display box 30 (S-9).

When a second measurement value T2 (24.85 mm) is obtained, a group D2 is set with reference to the measurement value T2. The measurement value which falls within the group D2 includes T2 only. Accordingly, the number Nn is one, and the measurement value T1 remains as effective data in the step S-11.

When a third measurement value T3 (25.08 mm) is obtained, a group D3 is set with reference to the measurement value T3. The measurement value which falls within the group D3 includes T1 and T3. Accordingly, the number Nn is two. Then, the effective data is renewed with the number Nn of the measurement values (the number Nmax is also renewed with two). Then, the measurement values T1 and T3 are displayed in the display box 30.

When a fourth measurement value T4 (25.29 mm) is obtained, a group D4 is set with reference to the measurement value T4. The measurement value which falls within the group D4 includes T4 only. At this time, the measurement values T1 and T3 which fall within the group D3 and were previously determined as the effective data are kept being displayed.

When a fifth measurement value T5 is obtained, a group D5 is set with reference to the measurement value T5. The measurement value which falls within the group D5 includes T4 and T5. Accordingly, the number Nn is two. In this case, the number Nmax of the effective data is the same as the number Nmax, two, of the effective data (T1, T3) in the group D3. At this time, the effective data (T1, T3) in the group D3 remains as the effective data in the step S-11. The same manner is applied to a case where a sixth measurement value T6 is obtained.

Next, a description of a case where a seventh measurement value T7 (25.17 mm) is obtained will be provided. The measurement values which fall within a group D7 set to have a width ΔD of permissible dispersion with reference to the measurement value T7 includes T3, T5 and T7. The number Nn is three. The number Nn is larger than the number Nmax, two, of the measurement values which fall within the group D3 previously determined as the effective data. Accordingly, the effective data is renewed with the measurement values T3, T5 and T7 in the group D7. Then, the number Nmax is renewed with three, and the measurement values T3, T5 and T7 are displayed in the display box 30.

Hereinafter, when a fifteenth measurement value T15 is obtained through the same processing steps, the measurement values which fall within a group D15 set with reference to the measurement value T15 includes T4, T5, T6, T7, T8, T10, T11, T13, T14 and T15. When the number Nmax of the effective data reaches ten, which is the number Np, the measurement is terminated. The measurement values are displayed in the display box 30. In addition, when the measurement is terminated, the control part 10 which functions as central value calculating means (a central value calculating unit) calculates an average value as a central value, a standard deviation and other values based on the ten measurement values which are determined as the effective data. Then, calculation results thereof are displayed in the display box 31.

Here, a description of the example in FIG. 5 in a case where a conventional processing method is employed will be provided. The measurement value T3 is regarded as effective with respect to the width ΔD of the permissible dispersion which is set with reference to the first measurement value T1. However, the measurement values T4, T5 and T6 are successively regarded as ineffective data with respect to the same. Accordingly, the data is abandoned. Then, it is judged whether the subsequently obtained measurement values are effective or ineffective with respect to the width ΔD of the permissible dispersion which is newly set with reference to the measurement value T7. When the fifteenth measurement value T15 is obtained, the effective data which falls within the width ΔD of the permissible dispersion with reference to the measurement value T7 includes the six measurement values of T7, T8, T12, T13, T14 and T15. Then, the measurement continues thereafter.

Figure 4:
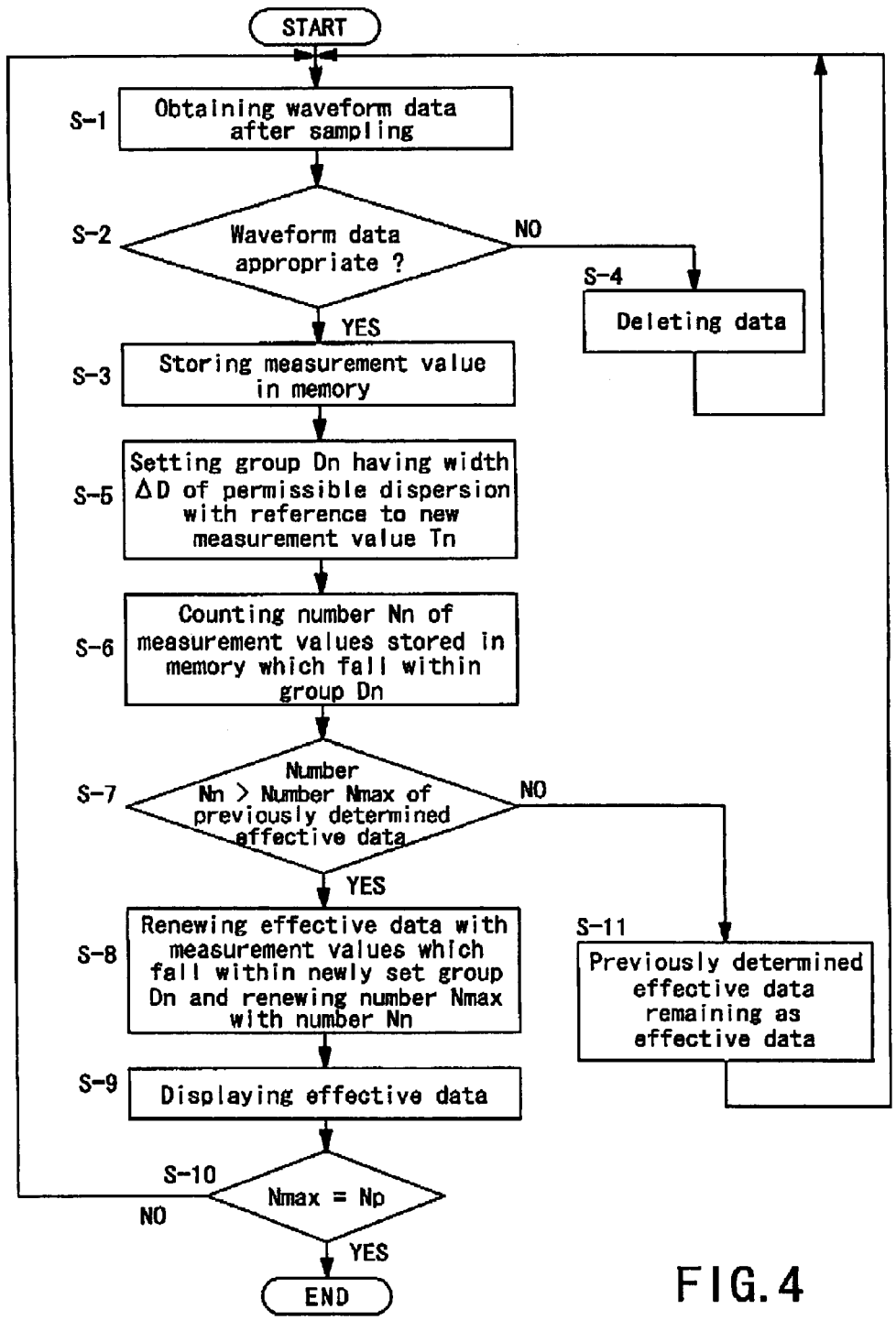
FIG. 4 is a flowchart of the first embodiment.
Figure 5:
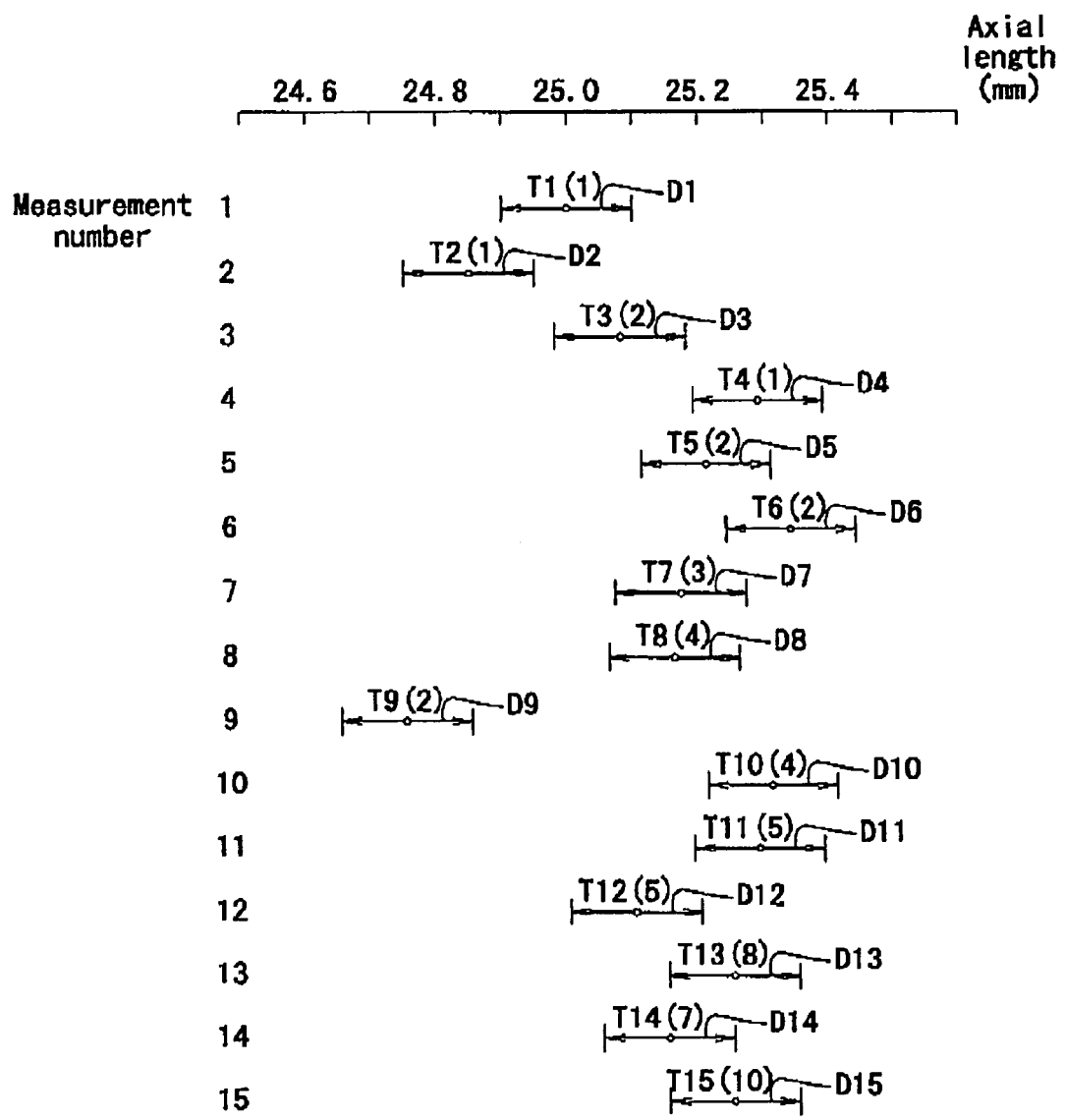
FIG. 5 is a graph showing measurement results of the first embodiment.

Meanwhile, by performing the measurement in accordance with the processing flow in FIG. 4, the effective data which falls within the width ΔD of the permissible dispersion can be obtained in large numbers at an early stage as described above. Accordingly, the measurement results with high reliability are obtained without lengthy measurement.

A description of a case where the number Nn and the number Nmax are equal in the comparison between the number Nn and the number Nmax of the previously determined effective data in the step S-7 in FIG. 4 will be provided. In this case, the processing step may proceed to the step S-8 (a step in which the effective data is renewed with the measurement values which fall within the newly set group Dn, and the number Nmax is renewed with the number Nn), not proceeding to the step S-11 in which the previously determined effective data remains as the effective data. However, the frequent change of the measurement values displayed in the display box 30 on the display panel 3 may give the examiner (user) the impression of being troublesome. Accordingly, the processing step of proceeding to the step 11 is employed in the preferred embodiment of the present invention. Alternatively, measurement values having a smaller standard deviation may be determined as the effective data. The selection concerning which group of the measurement values is determined as the effective data when the number Nn and the number Nmax are equal may be arranged to be made by the examiner by providing selection means on the display panel 3.

Second Embodiment of Automatic Termination Program

Figure 6:
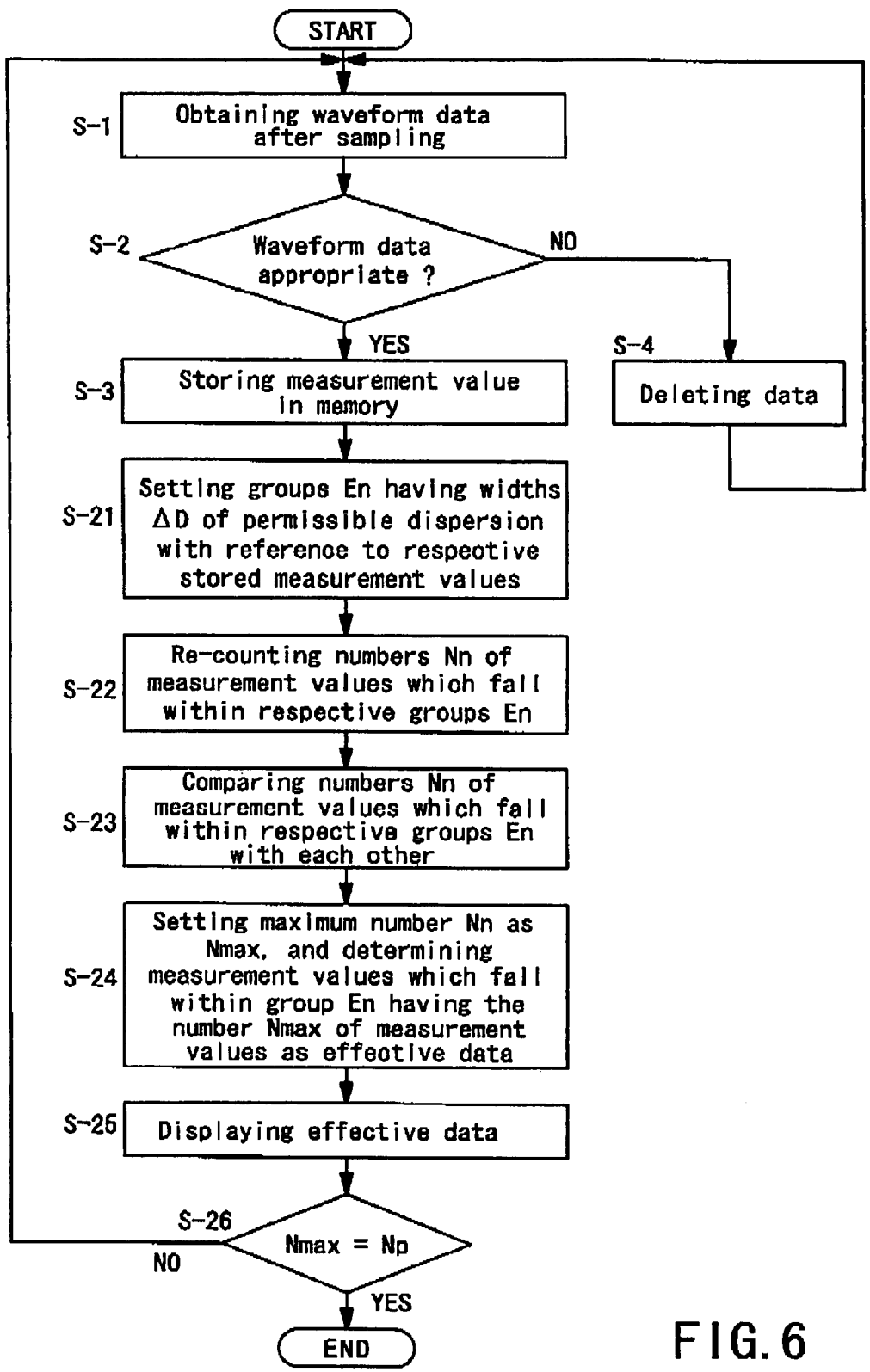
FIG. 6 is a flowchart of the second embodiment.
Figure 7:
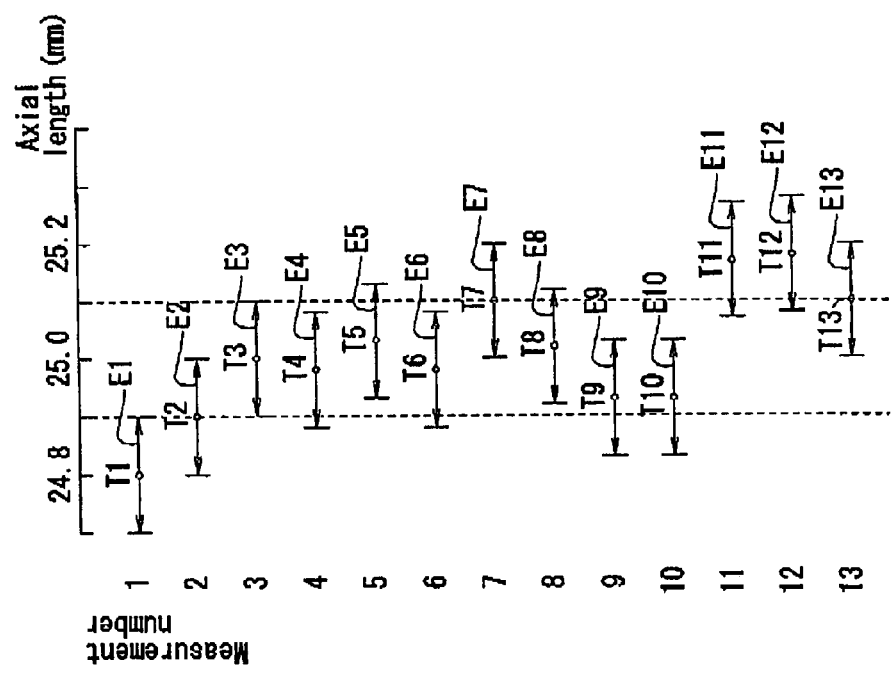
FIG. 7 is a graph showing measurement results of the second embodiment.

A description of the second embodiment of the automatic termination program will be provided based on a flowchart in FIG. 6 and a graph in FIG. 7. FIG. 7 is the graph in which measurement results are plotted at every obtainment of measurement values of the axial length, similarly to FIG. 5.

In the second embodiment, the step S-1 to step S-4 are the same as those in the flowchart of the first embodiment, and steps starting with a step S-21 mainly differ. In the steps starting with the step S-5 in the first embodiment, when the new measurement value Tn is obtained, the group Dn having the width ΔD of the permissible dispersion is set with reference to the measurement value Tn. Then, the number Nn of the measurement values which fall within the group Dn is counted and the effective data is determined by comparing the number Nn and the number Nmax of the previously determined effective data. In the second embodiment, when a new measurement value Tn is obtained, groups En having widths ΔD of permissible dispersion are firstly set with reference to the respective measurement values T1 to Tn (n=1, 2, 3, ...) stored in the memory 15 (S-21). Then, the numbers Nn of the measurement values which fall within the respective groups En are re-counted (S-22). Next, the numbers Nn of the measurement values in the respective groups En are compared with each other (S-23). Then, the maximum number Nn is set as Nmax, and the measurement values which fall within the group En having the number Nmax of the measurement values are determined as effective data (S-24). The subsequent steps S-25 and S-26 are the same as the steps S-9 and S-10 in the first embodiment.

A specific example by the graph in FIG. 7 will be described taking a case where a second measurement value T2 is obtained as an example. In this case, the measurement value which falls within a group E2 set with reference to the measurement value T2 includes the two measurement values of T1 and T2. In addition, the measurement value which falls within a group E1 set with reference to the measurement value T1 includes T1 and T2.

When a fourth measurement value T4 is obtained, the measurement value which falls within the group E1 set with reference to the measurement value T1 includes the two measurement values of T1 and T2. The measurement value which falls within the group E2 set with reference to the measurement value T2 includes the four measurement values of T1, T2, T3 and T4. The measurement value which falls within a group E3 set with reference to the measurement value T3 and a group E4 set with reference to the measurement value T4 includes the three measurement values of T2, T3 and T4 respectively. Accordingly, the respective numbers of the measurement values which fall within the groups E1, E2, E3 and E4 are compared when the fourth measurement value T4 is obtained, and the number of the measurement values which fall within the group E2 is four, which is the maximum number. The number Nmax is set as four which is the number of the measurement values which fall within the group E2, and the measurement values T1, T2, T3 and T4 are determined as effective data. The measurement values T1, T2, T3 and T4 which are determined as the effective data are displayed in the display box 30 on the display panel 3.

In this manner, the control part 10 sets the groups En having the widths ΔD (±0.1 mm) of the permissible dispersion with reference to the respective measurement values Tn at every obtainment of the new measurement value Tn. Then, with respect to all the measurement values T1 to Tn stored in the memory 15, the numbers Nn of the measurement values which fall within the respective groups En are re-counted. As a result, the control part 10 determines the measurement values which fall within the group En having the number Nn which is the maximum number as the effective data. If the pattern such that the number Nn is the maximum number is more than one, it is preferable that a pattern such that the measurement values displayed in the display box 30 change less is determined as the effective data for the above-mentioned reason. Alternatively, a pattern such that the standard deviation is smaller may be determined as the effective data.

FIG. 8 is a graph showing results of the number Nn of the measurement values which fall within the respective groups E1 to E13 which are set with reference to the respective measurement values until a thirteenth measurement value T13 is obtained. In FIG. 8, the vertical axis indicates the number which specifies the group En, and the horizontal axis indicates the number which specifies the measurement value Tn. The results in FIG. 8 show that when the measurement value T13 is obtained, the measurement value which falls within the group E13 set with reference to the measurement value T13 includes the seven measurement values. Besides, the number of the measurement values which fall within the group E3 set with reference to the measurement value T3 includes the ten measurement values, which is the maximum number. In the group E3, the number of the measurement values which fall therewithin reaches ten, that is the measurement termination condition Np. Accordingly, the measurement is terminated when the measurement value T13 is obtained.

Using the processing method of the second embodiment makes calculation processing more complicated than that of the above-mentioned first embodiment. However, the measurement result with high reliability can be obtained in a shorter measurement time (with the less number of times of measurement).

Third Embodiment of Automatic Termination Program

Figure 10:
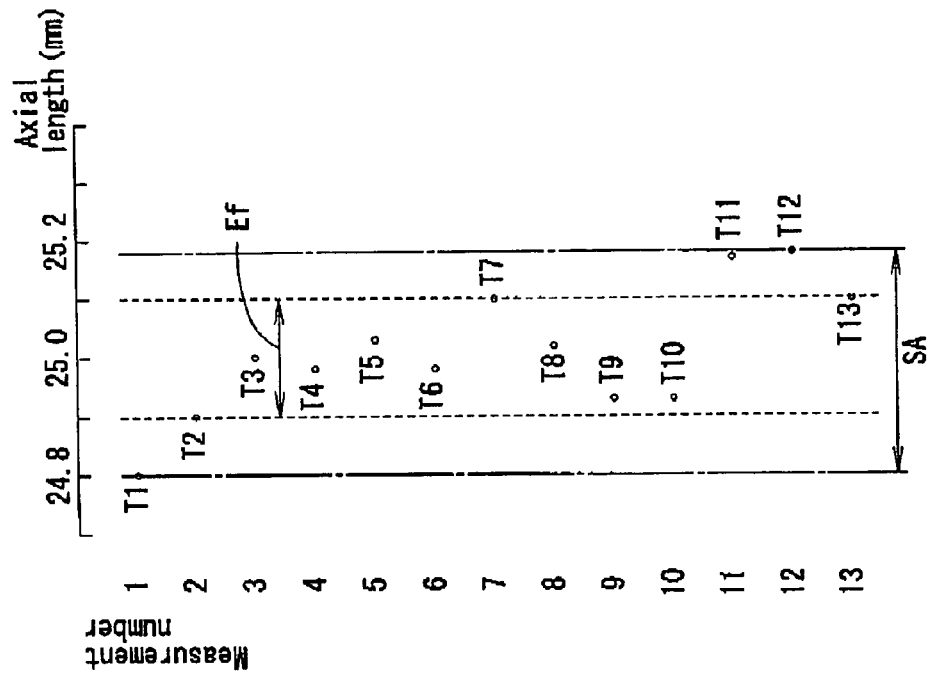
FIG. 10 is a graph showing measurement results of the third embodiment.
Figure 9:
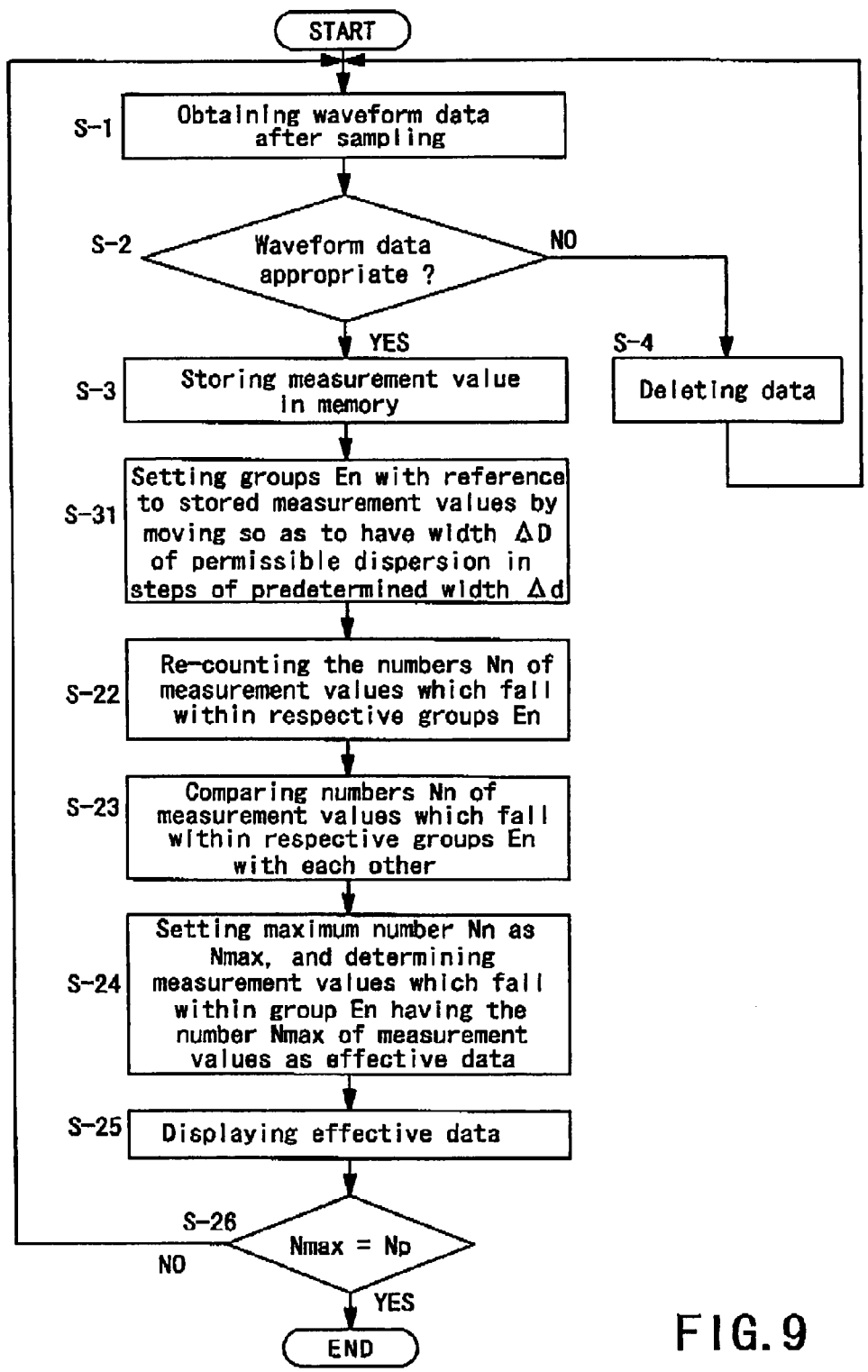
FIG. 9 is a flowchart of the third embodiment.

The third embodiment of the automatic termination program is described based on a flowchart in FIG. 9 and a graph in FIG. 10. FIG. 10 is the graph in which measurement results are plotted at every obtainment of measurement values of the axial length, similarly to FIG. 5 and FIG. 7.

In FIG. 9, the step S-1 to step S-4 are the same as those of the second embodiment, and steps starting with a step S-31 differ. In the step S-31 in the third embodiment, setting of the width ΔD (±0.1 mm) of the permissible dispersion with reference to the measurement value Tn is not made. Instead, when a now measurement value Tn is obtained, a plurality of groups En are set with reference to the measurement values stored in the memory 15 by moving so as to have the width ΔD (a width of 0.2 mm in this case) of the permissible dispersion in steps of a predetermined width Δd. The subsequent steps are the same as steps starting with the step S-22 in the second embodiment. That is to say, first, the numbers Nn of the measurement values which fall within the respective groups En are recounted (S-22). Next, the numbers Nn of the measurement values in the respective groups En are compared with each other (S-23). Then, the maximum number Nn is set as Nmax, and the measurement values which fall within the group En having the number Nmax of the measurement values are determined as the effective data (S-24).

A range of setting the groups En will be described taking the case where the measurement values T1 to T13 are obtained as an example. Here, the range between the shortest length among the measurement values T1 to T13 (the shortest length is the measurement value T1 in FIG. 10) and the longest length among the measurement values T1 to T13 (the longest length is the measurement value T12 in FIG. 10) is set as a range SA. In addition, it is essential only that the width Δd of the step in which the range SA is moved so as to have the width ΔD of the permissible dispersion is set as, for example, 0.01 mm, 0.05 mm and 0.10 mm in consideration of a relationship between reliability in measurement and a calculation processing speed.

In other words, in the processing step of the third embodiment, the control part 10 moves a box having the width ΔD (a width of 0.2 mm) of the permissible dispersion in the range SA in which the measurement values Tn are obtained in the steps of the predetermined width Δd, and then searches an area within which the measurement values fall the most.

The measurement values T1 to T13 which are obtained at the respective numbers of the measurement in FIG. 10 are identical with those in FIG. 7. As shown in FIG. 10, when the measurement values T1 to T13 are obtained, a group Ef which has the width ΔD of the permissible dispersion taking the vicinity of the measurement value T3 as the center is determined as the area within which the maximum number of the measurement values fall. In this case, the measurement values which fall within the group Ef are determined as effective data and are displayed in the display box 30 (S-25). Then, since the number of the measurement values which fall within the group Ef reaches ten, the measurement is terminated (S-26).

Fourth Embodiment of Automatic Termination Program

Figure 11:
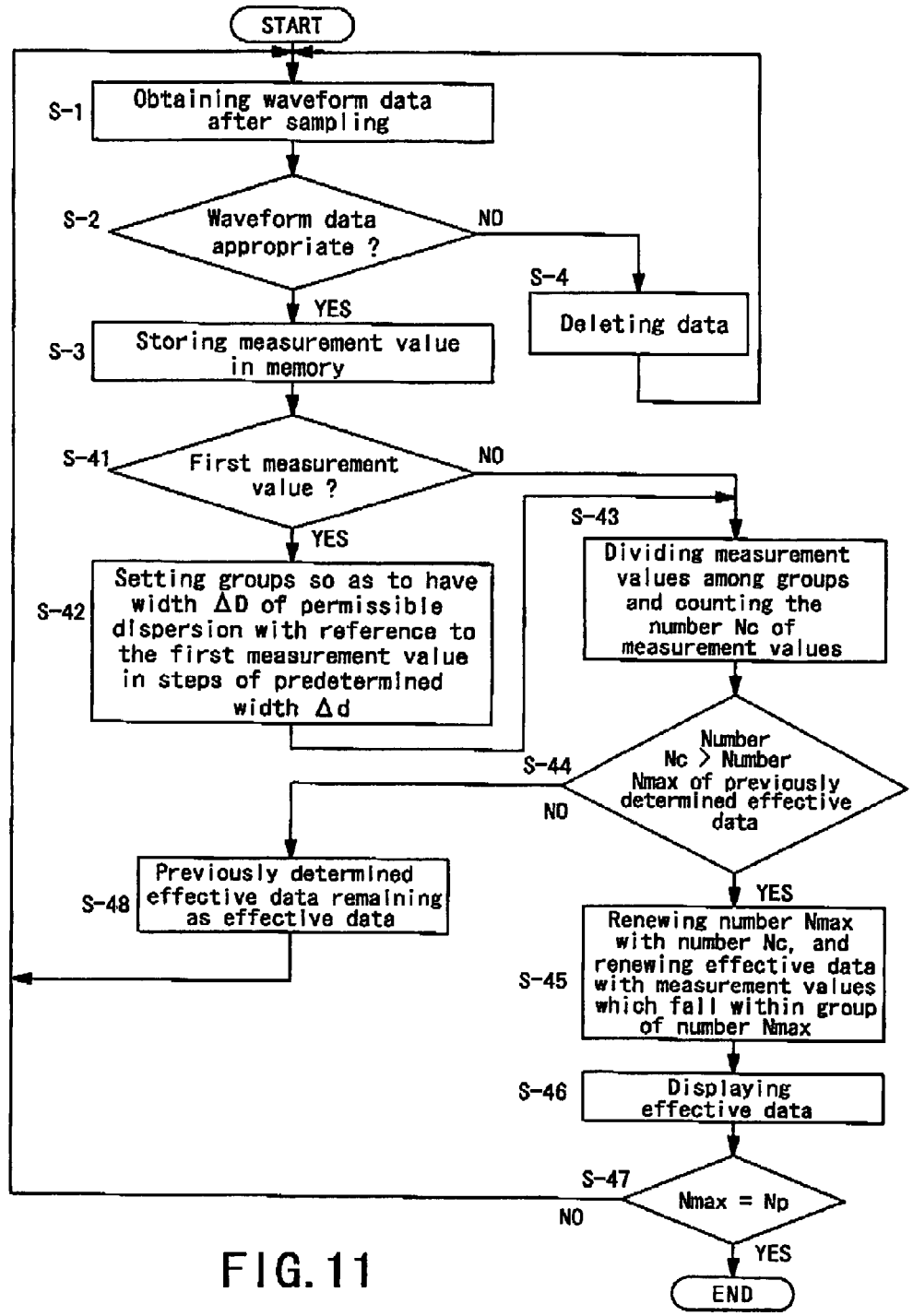
FIG. 11 is a flowchart of the fourth embodiment.
Figure 12:
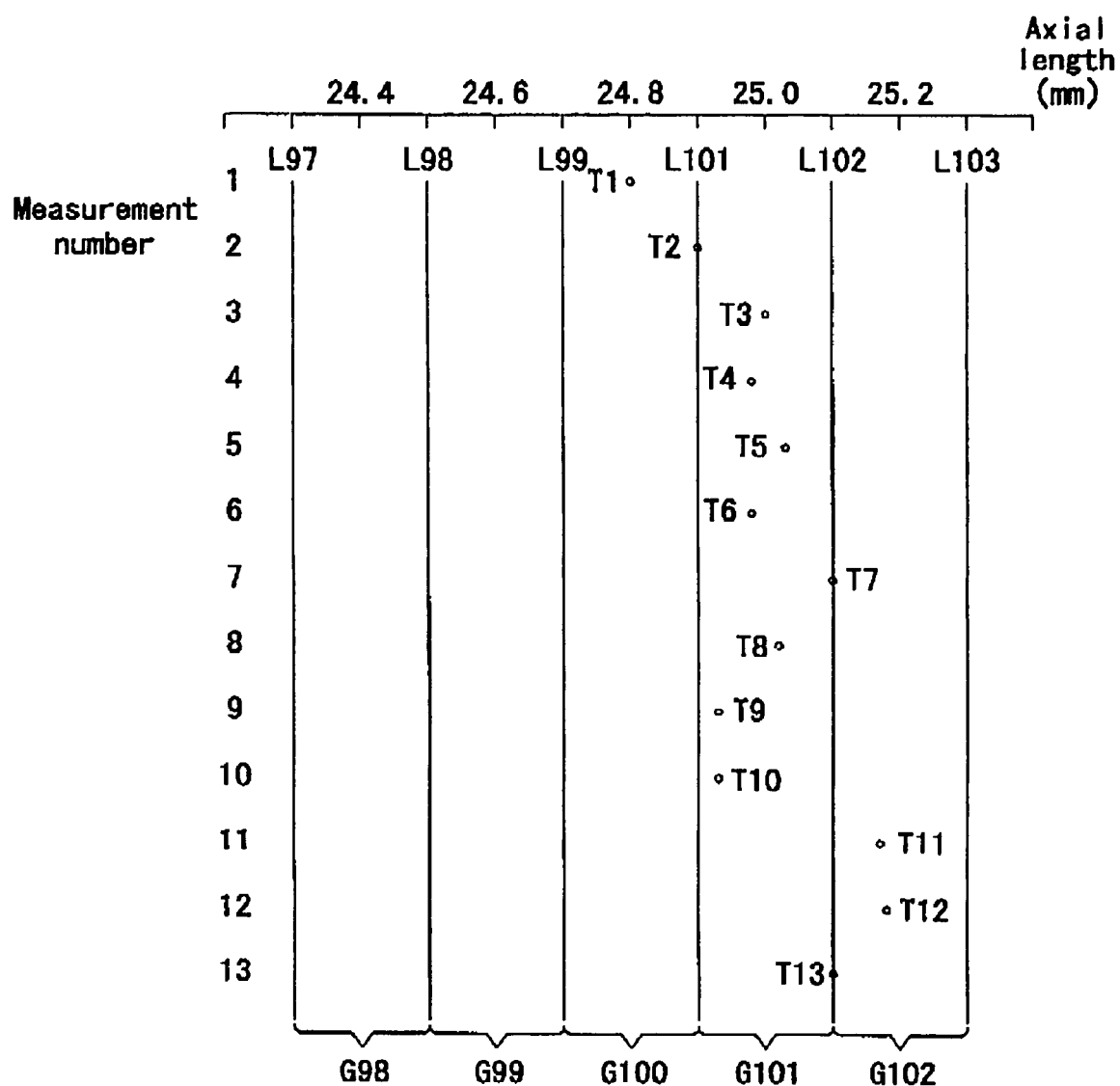
FIG. 12 is a graph showing measurement results of the fourth embodiment.

A description of the fourth embodiment of the automatic termination program will be provided based on a flowchart in FIG. 11 and a graph in FIG. 12. FIG. 12 is the graph in which measurement results are plotted at every obtainment of measurement values of the axial length, similarly to FIG. 7 and others. In FIG. 11, the steps S-1, S-2, S-3 and S-4 are the same as those of the other embodiments.

The fourth embodiment resembles especially the third embodiment. Hereinafter, a description of differences between the fourth embodiment and the other embodiments will be mainly provided. The control part 10 judges whether or not the measurement values stored in the memory 15 is the first obtained one (S-41). In the case of the first measurement value T1, the control part 10 sets a plurality of groups so as to have the width ΔD (the width of 2 mm) of the permissible dispersion with reference to the measurement value T1 (taking the measurement value T1 as the center) in the steps of the predetermined width ad (S-42). In FIG. 12, the step of the width ad is set as 0.2 mm which is the same as the width ΔD of the permissible dispersion. Then, the control part 10 sets a boundary L99 on the line at −0.1 mm side with reference to the measurement value T1. In addition, a boundary L101 is set on the line at +0.1 mm side with reference to the same. Boundaries L98, L97 . . . are set in a direction where lengths of the measurement values become shorter than the boundary L99. Further, boundaries L102, L103 . . . are set in a direction where the lengths of the measurement values become longer than the boundary L101. Among the groups divided by the boundaries, the group including the first measurement value T1 is set as G100. Groups G99, G98 . . . are set in a direction where the axial length is below the group G100. In addition, groups G101, G102 . . . are set in a direction where the axial length is over the group G100.

Next, the first measurement value T1 and the subsequent measurement values are divided respectively among the groups set in the step S-42. Then, the control part 10 counts the number Nc of the measurement values which fall within the divided groups (S-43). Besides, if the measurement value falls on the boundary between the two groups (like the measurement value T2 falling on the boundary L101), the measurement value belongs to both the groups (in the case of the measurement value T2, it belongs to both of the group G100 at left and the group G101 at right). If the measurement value falling on the boundary belongs to either one of the groups at right and at left, or belongs to neither of the groups, the number of times of measurement which should be performed until the measurement termination increases. Accordingly, the measurement takes time until its termination. For this reason, it is preferable that in order to count the approximate measurement values as many as possible, the measurement values are arranged to belong to both the groups at right and at left.

Next, the control part 10 compares the number Nc with the number Nmax of the previously determined effective data so as to know whether the number Nc is larger than the number Nmax S-44). If the number NC is larger than the number Nmax, the number Nmax is renewed with the number Nc. Then, the effective data is renewed with the measurement values which fall within the group of the number Nmax (S-45). There is no effective data previous to the first measurement value T1 that belongs to the group G100. Accordingly, in the step S-45, the measurement value T1 is determined as the effective data. When the second measurement data T2 is obtained, the number NC of the measurement values in the group G100 counts two, which are determined as the effective data. The effective data is displayed in the display box 30 (S-46). If the number Nmax of the effective data does not reach the measurement termination number Np (ten), the measurement continues (S-47). If the number Nc is smaller than the number Nmax in the step S-44, the previously determined effective data remains as the effective data (S-48).

Then, the effective data is determined through the similar processing. When the number Nmax of the effective data reaches ten, the measurement is terminated. In the example in FIG. 12, when the thirteenth measurement value T13 is obtained, the measurement value T13 is divided so as to fall within the group G101. When the number of the measurement values which belong to the group G101 reaches ten, the measurement is terminated. Also in the fourth embodiment, the measurement values stored in the memory 15 which are determined as ineffective data are not abandoned. Then, the control part 10 determines the effective data according to the number of the measurement values which fall within the group set so as to have the width ΔD of the permissible dispersion. Accordingly, compared with the prior art, measurement result with higher reliability can be obtained in a short time.

Incidentally, in the above-described fourth embodiment, in order to facilitate the calculation, the step of the width Δd in which the groups G are set is set as 0.2 mm which is the same as the width ΔD of the permissible dispersion. The step of the width ad may be set as 0.1 mm or 0.05 mm so as to have portions in which the respective groups overlap with each other. In this case, the groups are divided into smaller sections and one measurement value belongs to a plurality of the groups. Accordingly, the possibility that the number Nmax satisfies the number Np at a stage with the smaller number of times of the measurement is enhanced, which allows the measurement result with higher reliability to be obtained much earlier.

In the fourth embodiment, the first measurement value is set as a reference in setting the group G in the step S-41. However, since a range of the axial length of the human eye is known to some extent, the plurality of the groups G may be set previously.

A standard deviation a may be applied to the width AD of the permissible dispersion in any embodiments described above. In addition, the measurement of the present invention can be applied to measurement of a corneal thickness, a depth of the anterior chamber, a thickness of the crystalline lens, a length of the vitreous body, and other length in addition to the axial length.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic ultrasonic diagnostic apparatus which measures constituent parts of an examinee's eye through A-mode, the apparatus comprising:
   an ultrasonic probe for A-mode measurement including a transducer which emits an ultrasonic wave into the examinee's eye, and receives echoes reflected respectively from tissues of the constituent parts;
   calculation means for judging whether signals of the received reflected echoes are appropriate by analyzing the reflected echo signals and calculating measurement values of the constituent parts based on the reflected echo signals which are judged as appropriate;
   a memory which stores the calculated measurement values;
   grouping means for setting grouping ranges each having a predetermined permissible dispersion range with reference to the measurement value, and determining that either one of;
   the grouping range which is previously set; and
   the grouping range which is newly set based on the obtained measurement value; and
   central value calculating means for counting the number of the measurement values which fall within the respective grouping ranges, and calculating a central value based on the measurement values which fall within the grouping range such that the number of the measurement values falling within the grouping range reaches a predetermined number.

2. The ophthalmic ultrasonic diagnostic apparatus according to claim 1, wherein the grouping means sets the grouping ranges with reference to the measurement value which is obtained first.

3. The ophthalmic ultrasonic diagnostic apparatus according to claim 1, wherein the grouping means sets the grouping ranges in steps of a predetermined width in a range including the lowest and highest measurement values stored in the memory.

4. The ophthalmic ultrasonic diagnostic apparatus according to claim 1, wherein the grouping means sets the grouping ranges with reference to the measurement values at every obtainment of the measurement values.

5. An ophthalmic ultrasonic diagnostic apparatus which measures constituent parts of an examinee's eye through A-mode, the apparatus comprising:
   an ultrasonic probe for A-mode measurement including a transducer which emits an ultrasonic wave into the examinee's eye, and receives echoes reflected respectively from tissues of the constituent parts;
   a calculation unit which judges whether signals of the received reflected echoes are appropriate by analyzing the reflected echo signals and calculates measurement values of the constituent parts based on the reflected echo signals which are judged as appropriate;
   a memory which stores the calculated measurement values;
   a grouping unit which sets grouping ranges each having a predetermined permissible dispersion range with reference to the measurement value, and determines that either one of;
   the grouping range which is previously set; and
   the grouping range which is newly set based on the obtained measurement value; and
   a central value calculating unit which counts the number of the measurement values which fall within the respective grouping ranges, and calculates a central value based on the measurement values which fall within the grouping range such that the number of the measurement values falling within the grouping range reaches a predetermined number.

6. The ophthalmic ultrasonic diagnostic apparatus according to claim 5, wherein the grouping unit sets the grouping ranges with reference to the measurement value which is obtained first.

7. The ophthalmic ultrasonic diagnostic apparatus according to claim 5, wherein the grouping unit sets the grouping ranges in steps of a predetermined width in a range including the lowest and the highest measurement values stored in the memory.

8. The ophthalmic ultrasonic diagnostic apparatus according to claim 5, wherein the grouping unit sets the grouping ranges with reference to the measurement values at every obtainment of the measurement values.

* * * * *